(12) United States Patent
Kim et al.

(10) Patent No.: US 7,276,251 B2
(45) Date of Patent: Oct. 2, 2007

(54) SUSTAINED-RELEASE COMPOSITION OF DRUGS ENCAPSULATED IN MICROPARTICLES OF HYALURONIC ACID

(75) Inventors: Myung-Jin Kim, Daejeon (KR); Sun-Jin Kim, Seoul (KR); Oh-Ryong Kwon, Daejeon (KR)

(73) Assignee: LG Life Sciences, Ltd., Inc., Seoul (KR)

( * ) Notice: Subject to any disclaimer, the term of this patent is extended or adjusted under 35 U.S.C. 154(b) by 389 days.

(21) Appl. No.: 10/205,954

(22) Filed: Jul. 26, 2002

(65) Prior Publication Data

US 2002/0197328 A1    Dec. 26, 2002

Related U.S. Application Data

(63) Continuation-in-part of application No. 09/596,593, filed on Jun. 19, 2000, now abandoned, which is a continuation-in-part of application No. 09/194,653, filed on Nov. 30, 1998, now abandoned.

(30) Foreign Application Priority Data

Apr. 1, 1997    (KR)  ............................. 1997/12046

(51) Int. Cl.
*A61K 9/19*    (2006.01)
*A61K 9/22*    (2006.01)

(52) U.S. Cl. ................... 424/468; 424/489; 424/499; 424/502; 536/1.11; 514/2; 514/12; 514/13; 514/14; 514/23; 514/951; 530/300; 530/303; 530/311; 530/312; 530/313; 530/314; 530/315; 530/316; 530/317; 530/324; 530/325; 530/326; 530/350; 530/387.1; 530/388.1; 530/399

(58) Field of Classification Search ............ 514/2, 514/12, 13, 14, 23, 951; 530/300, 303, 311, 530/312, 313, 314, 315, 316, 317, 324, 325, 530/326, 350, 399, 387.1, 388.1, 1.11; 424/489, 424/468, 499, 502; 536/1.11
See application file for complete search history.

(56) References Cited

U.S. PATENT DOCUMENTS

| | | | | | |
|---|---|---|---|---|---|
| 4,971,782 | A | * | 11/1990 | Rudy et al. | ................... 424/53 |
| 5,622,657 | A | * | 4/1997 | Takada et al. | ............. 264/4.32 |
| 5,641,749 | A | * | 6/1997 | Yan et al. | ..................... 514/12 |
| 5,707,644 | A | * | 1/1998 | Illum | ........................ 424/434 |
| 5,753,234 | A | * | 5/1998 | Lee et al. | ................ 424/204.1 |
| 6,066,340 | A | * | 5/2000 | Callegaro et al. | ........... 424/499 |
| 6,375,988 | B1 | * | 4/2002 | Suzuki et al. | ............... 424/499 |

FOREIGN PATENT DOCUMENTS

| | | |
|---|---|---|
| EP | 0 486 959 A1 | 11/1991 |
| JP | 01-287041 A | 11/1989 |
| JP | 02-213 A | 1/1990 |

OTHER PUBLICATIONS

Kitano et al. (JP-2-213), published Jan. 05, 1990. Translation of JP-2-213.*
Patent Abstract of Japan; Patent No. 1992-283510; published Oct .8, 1992.
Patent Abstract of Japan; Patent No. 1993-186362; published Jul. 27, 1993.
Patent Abstract of Japan; Patent No. 1993-186364; published Jul. 27, 1993.
Patent Abstract of Japan; Patent No. 1997-309843; published Dec. 2, 1997.
Abstracts from National Library of Medicine re S.P. Zhong; "Biodegradation of hyaluronic acid derivatives by hyaluronidase"; published in *Biomaterials*, vol. 15, No. 5, 1994, pp. 359-65.

* cited by examiner

*Primary Examiner*—Anish Gupta
(74) *Attorney, Agent, or Firm*—Sughrue Mion, PLLC (57) ABSTRACT

A sustained-release drug composition consisting essentially of microparticles of hyaluronic acid having a high molecular weight or an inorganic salt thereof and a protein or peptide drug encased in said microparticles, wherein the average size of said microparticles ranges from 0.1 to 40 μm.

11 Claims, 9 Drawing Sheets

SUSTAINED-RELEASE COMPOSITION OF DRUGS ENCAPSULATED IN MICROPARTICLES OF HYALURONIC ACID

CROSS REFERENCE TO RELATED APPLICATIONS

This application is a continuation-in-part (CIP) application of U.S. Ser. No. 09/596,593 filed on Jun. 19, 2000, now abandoned, which is a CIP application of U.S. Ser. No. 09/194,653 filed on Nov. 30, 1998, now abandoned.

FIELD OF THE INVENTION

The present invention relates to a sustained-release composition of a protein or peptide drug encapsulated in solid microparticles of high molecular weight hyaluronic acid or its salt; and to an injection formulation containing same.

BACKGROUND OF THE INVENTION

Protein or peptide drugs are usually administered by injection because of their sluggish absorption via oral administration. Once injected, their in vivo activities last only a short period of time and, for this reason, repeated injections must be administered when a long-term treatment is required. For example, treatment of children suffering from pituitary growth hormone deficiency is carried out by daily injections of recombinant human growth hormone over a period of more than 6 months. Accordingly, a sustained-release formulation which does not require cumbersome daily administrations is highly desirable in such applications.

A typical sustained-release formulation of a protein or peptide drug, e.g., human growth hormone, is prepared by encapsulating the drug in microparticles of a biodegradable polymer matrix material, which slowly releases the drug as the matrix material undergoes in vivo degradation. In this line, extensive studies have been conducted to develop biodegradable polymers suitable for use in sustained-release drug formulations, and biodegradable polyesters such as polylactide, polyglycolide, poly(lactide-co-glycolide), poly-ortho-ester and polyanhydride have been found to be effective in such use [M. Chasin and R. Langer, et al., *Biodegradable Polymers as Drug Delivery System,* Mercel Dekker (1990) and J. Heller, *Adv. Drug Del. Rev.,* 10, 163 (1993)].

Other studies have also been carried out to develop a sustained-release drug formulation using natural polymer materials such as gelatin, collagen, chitosan, carboxymethyl cellulose, alginate and hyaluronic acid. A natural polymer generally forms a gel when placed in an aqueous environment and this type of highly viscous gel matrix, through which the drug diffuses very slowly, has been used in formulating sustained-release drug compositions.

For example, U.S. Pat. No. 5,416,071 discloses a sustained-release injection formulation of erythropoietin employing a gel containing 0.01% to 3% hyaluronic acid; Japanese Patent Publication No. 1-287041(1989) describes a sustained-released injection formulation of insulin employing a gel formed with 1% hyaluronic acid; and Japanese Patent Publication No. 2-00213(1990) reports a sustained-release formulation of calcitonin, elcanonine or human growth hormone employing a gel containing 5% hyaluronic acid. Similarly, Meyer et al., have developed a sustained-release formulation of granulocyte colony stimulating factor employing a gel containing 0.5 to 4% hyaluronic acid [James Meyer, et al., *J. Controlled Release,* 35, 67 (1995)].

However, administration of such formulations by injection requires the use of a large bore syringe-needle because a gel containing a few % hyaluronic acid has a high-viscosity in the order of $10^7$ centipoise. Moreover, as the injected gel gets diluted by body fluid, its drug retaining ability is rapidly diminished, and as a result, the sustaining of the drug release lasts no more than 1 day. For instance, Japanese Patent Publication No. 1-287041(1989) discloses that when a sustained-release injection formulation insulin containing 1% hyaluronic acid was administered to rabbits, the therapeutic effect of suppressing the blood glucose level did not last more than 24 hours. Also, the drug concentration in blood was reported to decrease to less than $\frac{1}{10}$ of the initial concentration in less than 24 hours when test animals were injected with a formulation of 2% hyaluronic acid containing granulocyte colony stimulating factor [James Meyer, et al., *J. Controlled Release,* 35, 67(1995)] or a formulation of 1.5% hyaluronic acid containing interferon-α and plasma protein (U.S. Pat. No. 5,416,017). Accordingly, a sustained release drug formulation based on hyaluronic acid gels has the serious drawback that the drug release cannot be maintained for more than 24 hours.

Natural hyaluronic acid or an inorganic salt thereof dissolves only in water. Hyaluronic acid-benzyl ester HYAFF™, on the other hand, dissolves not in water but in an organic solvent, e.g., dimethylsulfoxide. Drug compositions, comprising solid microparticles of such hydrophobic hyaluronic acid derivatives and drugs encased therein have been prepared by the conventional emulsion-solvent extraction method [N. S. Nightlinger, et al., 9*Proceed. Intern. Symp. Control. Rel. Bioact. Mater.,* 22nd, Paper No. 3205 (1995); L. Ilum, et al., *J. Controlled Rel.,* 29, 133 (1994)]. Such preparation is typically carried out as follows: A protein drug is dispersed in a dimethylsulfoxide solution of hyaluronic acid-benzyl ester and the dispersion thus obtained is added to a mineral oil to form an emulsion. An organic solvent, e.g., ethylacetate, is added to the emulsion to extract dimethylsulfoxide; and microparticles consisting of the drug and hyaluronic acid-benzyl ester are recovered therefrom.

However, this method has the problem that the protein drug may be denatured through its contact with the organic solvent or with hydrophobic hyaluronic acid-benzyl ester. In fact, a microparticular composition of granulocyte macrophage-colony stimulating factor (GM-CSF) prepared by using a fully esterified hyaluronic acid derivative was reported to release only about 25% of GM-CSF during the first few days and none after 17 days [N. S. Nightlinger, et al., *proceed. Intern. Symp. Control. Rel. Bioact. Mater.,* 22nd, Paper No. 3205(1995)]. In this case, a major portion of the protein drug was lost, most likely due to denaturation thereof through its interaction with hyaluronic acid-benzyl ester and/or the organic solvent.

SUMMARY OF THE INVENTION

Accordingly, it is an object of the present invention to provide an improved sustained-release composition of a protein or peptide drug.

In accordance with one aspect of the present invention, there is provided a sustained-release drug composition consisting essentially of microparticles of hyaluronic acid having a high molecular weight or an inorganic salt thereof and a protein or peptide drug encased in said microparticles, wherein the average size of said microparticles ranges from 0.1 to 40 μm.

BRIEF DESCRIPTION OF DRAWINGS

The above and other objects and features of the present invention will become apparent from the following description of the invention taken in conjunction with the following accompanying drawings, wherein.

DETAILED DESCRIPTION OF THE INVENTION

The sustained-release composition of the present invention comprises solid microparticles of hyaluronic acid having a high molecular weight or a salt thereof and a protein or peptide drug encapsuled in said particles. This inventive composition is superior to conventional formulations based on hyaluronic acid gels in terms of release characteristics and easiness in handling: that is, an injection formulation prepared using the inventive microparticular composition is easier to inject because of its low viscosity, and the composition releases the drug in vivo at a constant rate over a longer period of time.

Further, the inventive composition is advantageous in that the denaturation of the drug does not occur until 100% thereof is released from the composition.

The microparticular composition of the present invention having an average particle size ranging from 0.1 to 40 μm, preferably from 0.1 to 10 μm may be prepared by spray-drying or freeze-drying an aqueous solution containing a protein or peptide drug and hyaluronic acid having a high molecular weight or its salt. If desired, a stabilizer may be added to the solution.

Exemplary drugs that may be used in preparing the solid microparticular composition of this invention include human growth hormone, bovine somatotropin, porcine somatotropin, growth hormone releasing hormone, growth hormone releasing peptide, granulocyte-colony stimulating factor, granulocyte macrophage-colony stimulating factor, macrophage-colony stimulating factor, erythropoietin, bone morphogenetic protein, interferon, insulin, atriopeptin-III, monoclonal antibody, TNF, macrophage activating factor, interleukin, tumor denaturing factor, insulin-like growth factor, epidermal growth factor, tissue plasminogen activator and urokinase.

Hyaluronic acid having a high molecular weight which may be suitably used in the present invention is hyaluronic acid having a molecular weight of more than 1,000,000, preferably 1,000,000 to 3,200,000, and more preferably 1,000,000 to 2,000,000.

Representative inorganic salts of hyaluronic acid that may be used in preparing the solid microparticular composition of this invention include sodium, potassium, lithium, calcium, ammonium, magnesium, zinc, copper and cobalt salts.

Some of the stabilizers usable in the present invent include polysaccharide, protein, amino acid, lipid, fatty acid, polyethylene glycol, inorganic salt and surfactant.

The microparticular sustained-release composition of the present invention may contain a protein or peptide drug in an amount ranging from 1 to 90 wt % based on the weight of the composition, and optionally, a stabilizer in an amount ranging form 1 to 90 wt % based on the weight of the composition.

The sustained-release injection formulation of the present invention is prepared by dispersing in an injection medium the microparticular sustained-release composition of the present invention in an amount ranging from 0.01 to 10 wt % based on the weight of the injection formulation. If desired, a dispersant or preservative may be added thereto. Typical injection media that may be used in the injection formulation of the present invention include a buffered aqueous solution, ethanol, propyleneglycol, polyethyleneglycol, vegetable oil, mineral oil, squalene, cod liver oil, monoglyceride, diglyceride and triglyceride or a mixture thereof.

Exemplary vegetable oils are corn oil, olive oil, soy bean oil, sunflower oil, cotton seed oil, peanut oil, sesame oil and a mixture thereof.

Further, an aerosol formulation containing the microparticular sustained release composition of the present invention may be prepared. The aerosol formulation of the present invention thus prepared may be applied to the nose or bronchi mucous membrane wherein the microparticular composition releases the drug in a controlled manner.

The following Examples and Test Examples are intended to further illustrate the present invention without limiting its scope.

EXAMPLE 1

Preparation of Microparticle

To a 5 mM phosphate buffered saline (PBS) containing 2 mg/ml of human growth hormone (hGH), Tween 80 was added to a concentration of 0.01 wt %. Sodium hyaluronate having a molecular weight of 1,000,000 was added thereto to a concentration of 2mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 μm.

EXAMPLE 2

Preparation of Microparticle

To a 5 mM PBS containing 1 mg/ml of hGH, Tween 80 was added to a concentration of 0.01 wt %. Sodium hyaluronate having a molecular weight of 2,000,000 was added thereto to a concentration of 1 mg/ml. The resulting solution was supplied to a spray-dryer (Büchi 190) at a rate of 2 ml/min. to prepare microparticles. The temperature of the influx air to the spray dryer was 85° C. The mean diameter of the microparticles thus obtained was 2.0 μm.

EXAMPLE 3

Preparation of Microparticle

To a 5 mM PBS containing 0.1 mg/ml of hGH, Tween 80 was added to a concentration of 0.01 wt %. Sodium hyaluronate having a molecular weight of 2,000,000 was added thereto to a concentration of 0.9 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 2.0 μm.

TEST EXAMPLE 1

In vitro Release-Test

The microparticles prepared in Examples 1, 2 and 3 were respectively suspended in a buffer (150 mM sodium chloride, 10 mM phosphate and 0.05% sodium azide, pH 7.4) so that a concentration of hGH becomes 1.0 mg/ml. The dispersion thus obtained was put in oven and the release of hGH was tested in a 37° C. stirrer. At the predetermined sampling time, the resulting dispersion was centrifuged at 800 g for 10 min. to obtain a supernatant and a fraction of the supernatant corresponding to 1/10 of the entire dispersion was removed therefrom. An equal amount of the buffer was added to the dispersion and the release-test was continued at 37° C.

The concentration of hGH in the supernatant fraction was measured by Lowry method and high performance liquid chromatography (HPLC) in order to determine the amount of released hGH relative to the time. The results are shown in FIG. 1.

Figure 1:
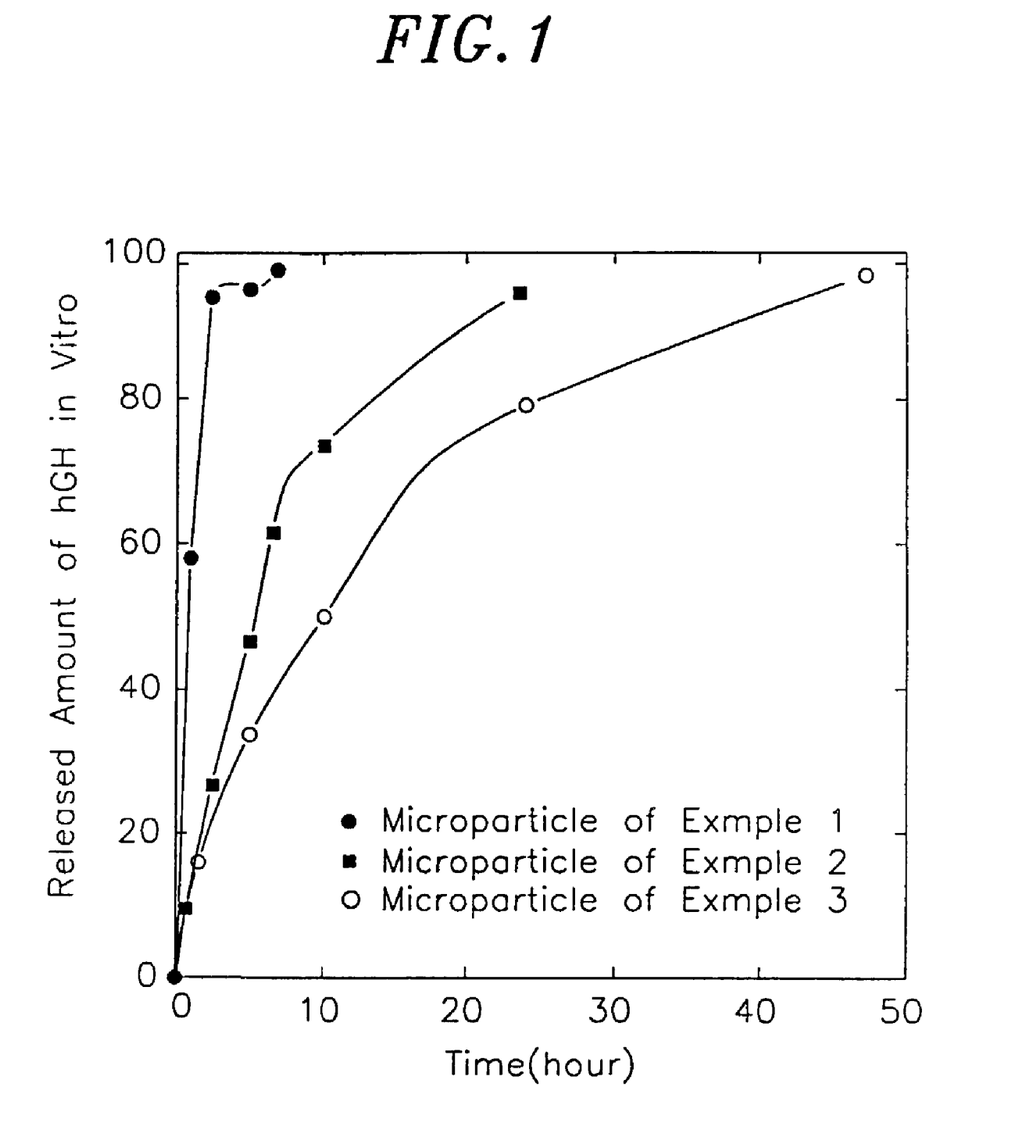
FIG. 1 displays the time-dependent changes in the released amount of human growth hormone (hGH) in vitro.

FIG. 1 displays the time-dependent changes in the released amount of hGH in vitro. As shown in FIG. 1, the rate of hGH release is slower as the molecular weight of hyaluronic acid is higher and the content of hGH is lower. In deed, the microparticle obtained in Example 3 shows slowest release rate. These results show that the period of sustained-release of the drug can be controlled by regulating the molecular weight of hyaluronic acid, the content of hGH and the like. Moreover, the microparticles prepared in the present invention exhibit constant rate of in vitro until 70% of hGH is released, without initial burst release.

TEST EXAMPLE 2

Stability of hGH in Microparticle

In order to confirm whether the hGH in the inventive microparticles is identical with the aqueous hGH used for the preparation of the microparticles, hGH released from the microparticles in the in vitro release test was assayed by employing reversed-phase high performance liquid chromatography (RP-HPLC) and size exclusion chromatography (SEC).

Figure 2A:
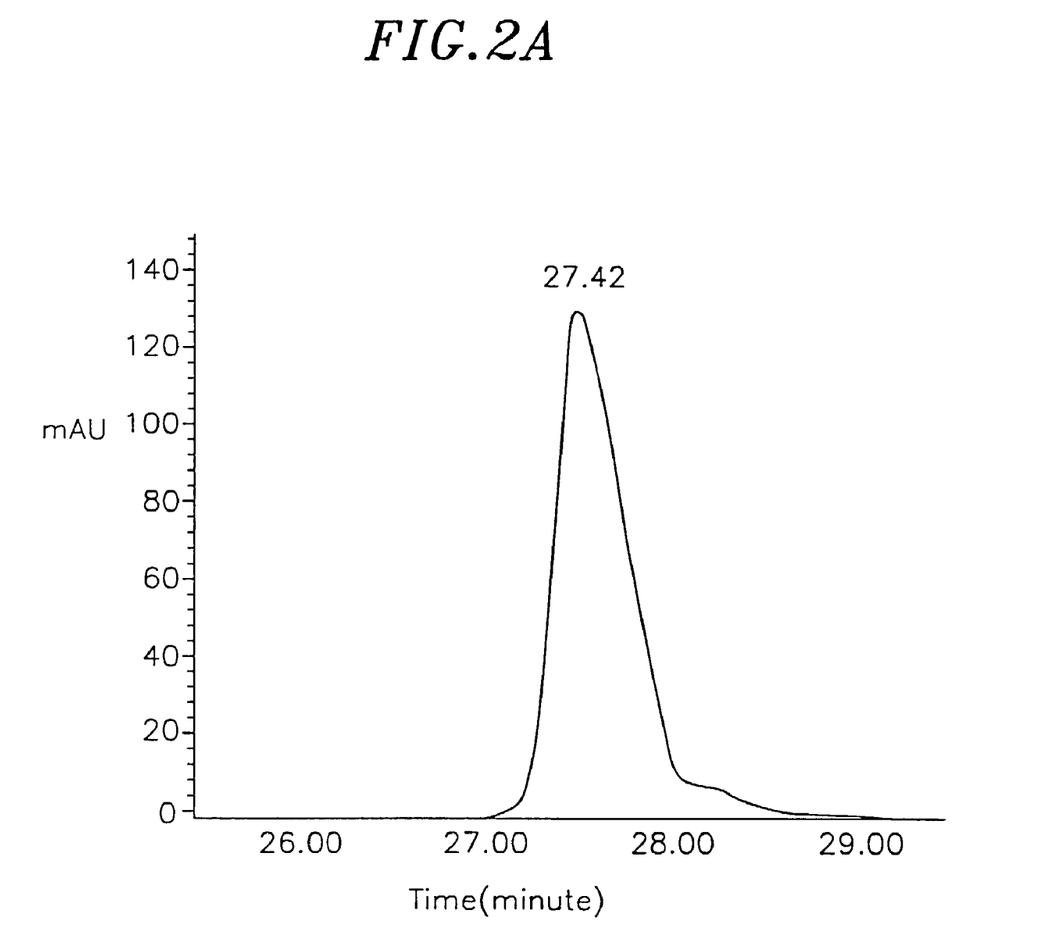
FIGS. 2A and 2B demonstrate the stability of the sustained-release composition of the present invention containing hGH by reversed phase high performance liquid chromatography (A: hGH released from the formulation of the present invention; and B: aqueous hGH Control)
Figure 2B:
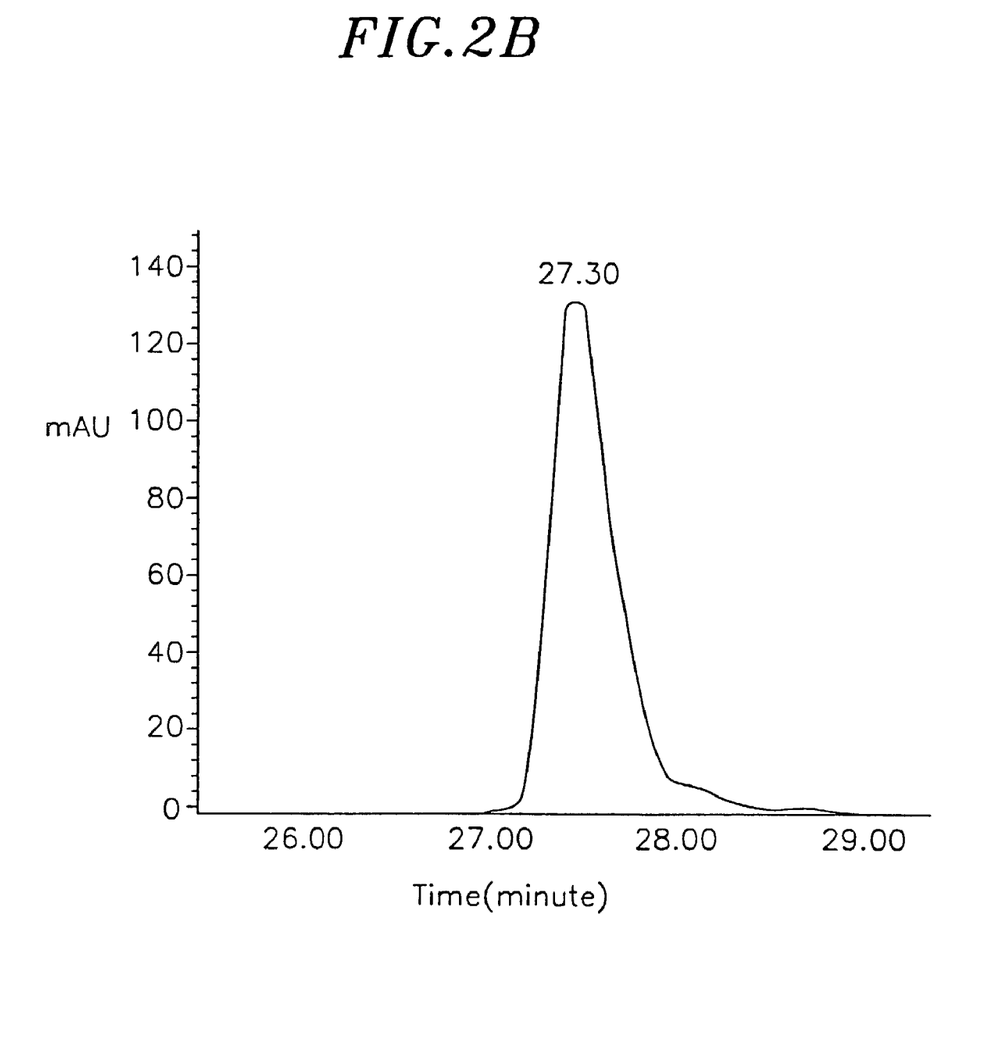

The denaturation of hGH due to the oxidation and deamidation can be confirmed by RP-HPLC and the results are shown in FIGS. 2A and 2B.

FIGS. 2A and 2B demonstrate the stability of the sustained-release composition of the present invention containing hGH by RP-HPLC, wherein FIG. 2A is the RP-HPLC profile of hGH released from the formulation of the present invention and FIG. 2B, aqueous hGH Control.

Figure 3A:
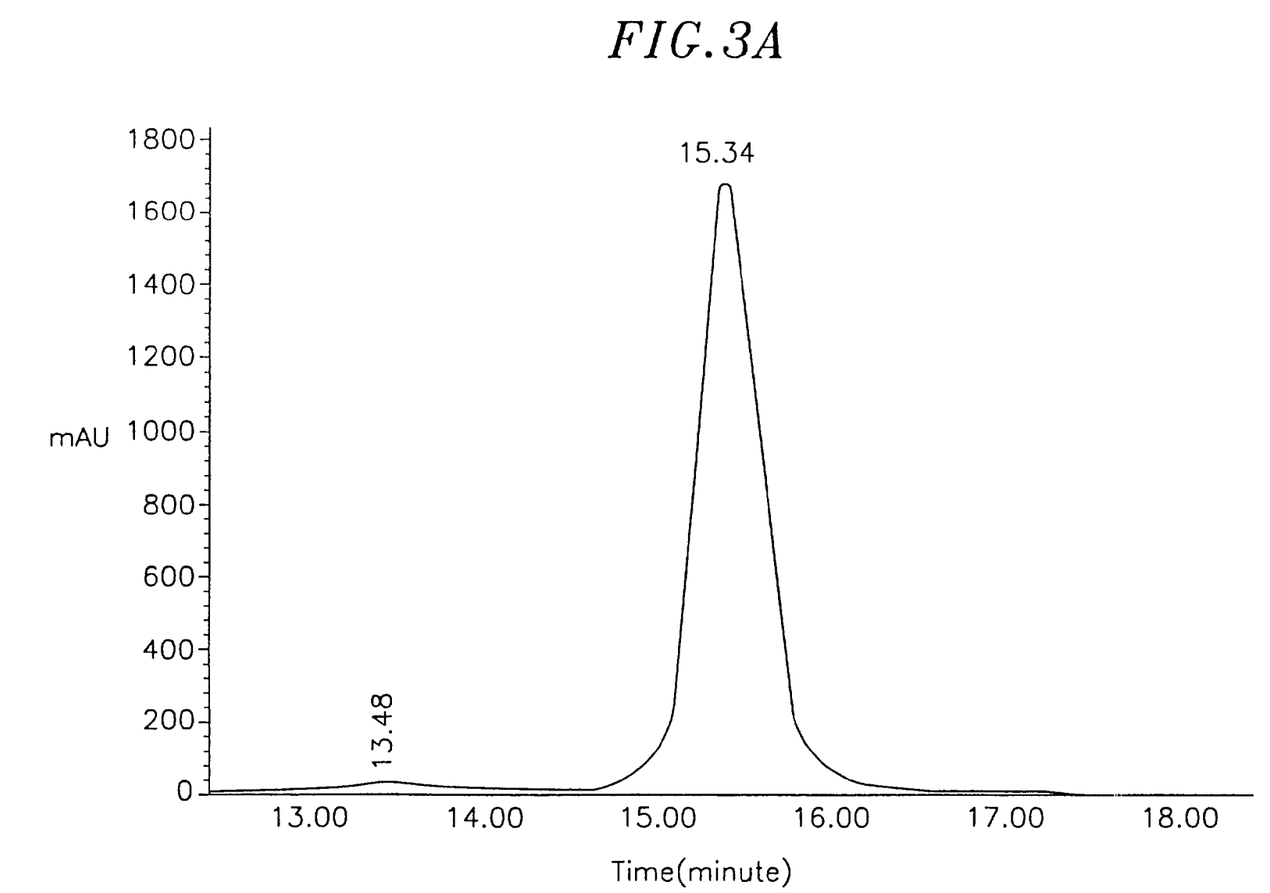
FIGS. 3A and 3B illustrate the stability of the sustained-release composition of the present invention containing hGH by size exclusion chromatography (A: hGH released from the formulation of the present invention and B: aqueous hGH Control)
Figure 3B:
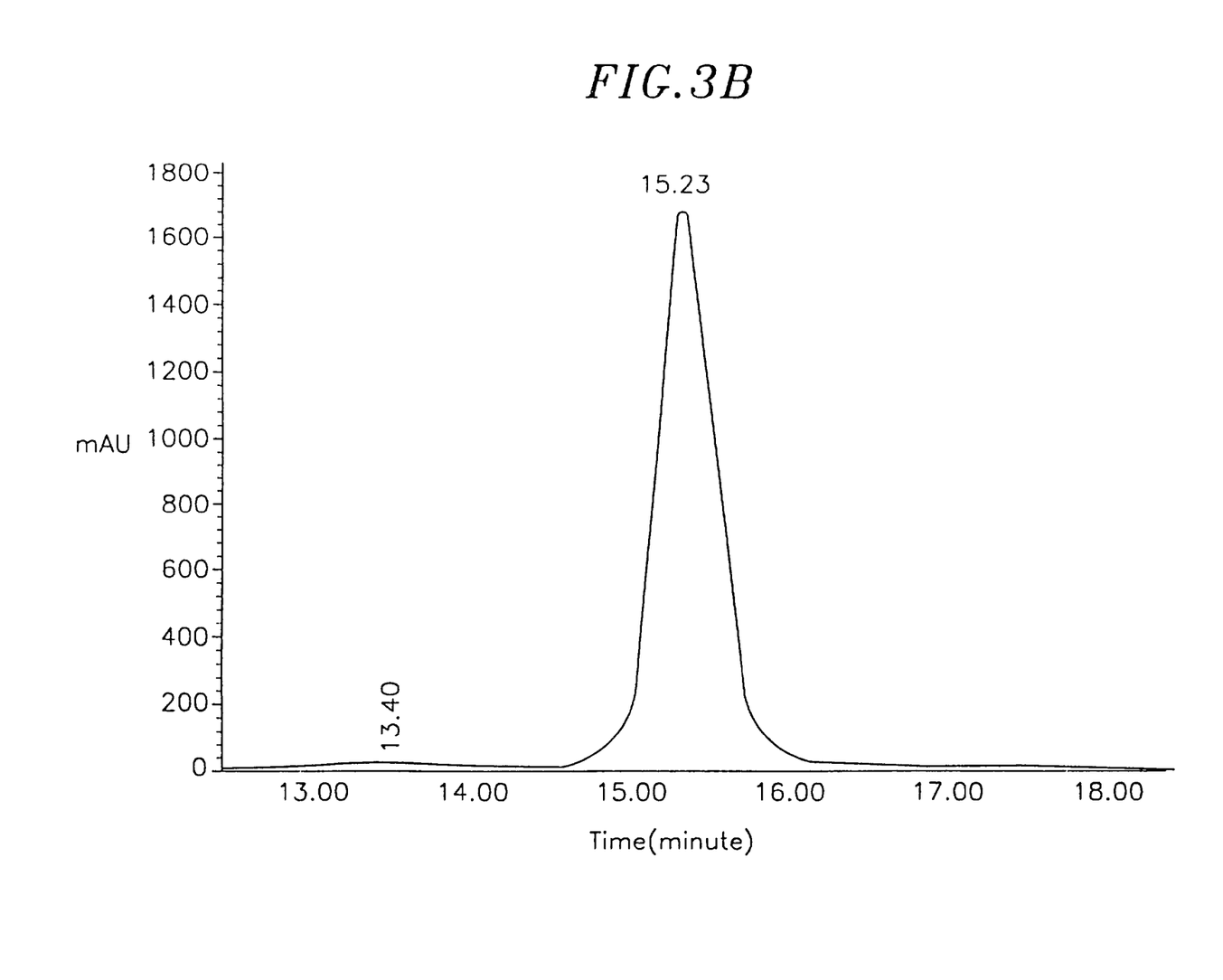

The denaturation of hGH due to the aggregation can be confirmed by SEC and the results are shown in FIGS. 3A and 3B.

FIGS. 3A and 3B demonstrate the stability of the sustained-release composition of the present invention containing hGH by SEC, wherein FIG. 3A is the SEC profile of hGH released from the formulation of the present invention and FIG. 3B, aqueous hGH Control.

As shown in FIGS. 2A, 2B, 3A and 3B, hGH released from the inventive compositions is identical with the aqueous hGH Control and the content of hGH monomer is more than 95%. These results show that the denaturation of hGH does not occurred during the preparation of the inventive microparticle compositions and the release thereof at 37° C.

TEST EXAMPLE 3

In vivo Release-Test

Dwarf rats having the heredity of low growth hormone secretion were employed in a test to examine the sustained-release property of the microparticle of the present invention.

The sustained-release microparticle prepared in Example 1 was dispersed in a mixture of propyleneglycol and ethanol (7:3(v/v)) so that the concentration of hGH became 5 mg/ml. The resulting dispersion was diluted with a buffered aqueous solution (150 mM NaCl and 10 mM phosphate, pH 7.4) so that a concentration of hGH became 0.5 mg/ml.

Eighteen heads of seven week-old dwarf rats having an average body weight of 103 g were divided into three groups, each consisting of six rats. The rats of the first group were administered by a subcutaneous injection with 0.1 ml of the microparticle dispersion prepared above (corresponding to 50 μg of hGH) daily for a period of two weeks (Experimental group). The rats of the second group were administered with Eutropin®, a commercially available hGH formulation for aqueous injection, under the same condition (Comparative group). The rats of the third group were not administered with hGH (non-treated Control group). The rats were weighted every day to examine the change in their body weight.

Figure 4:
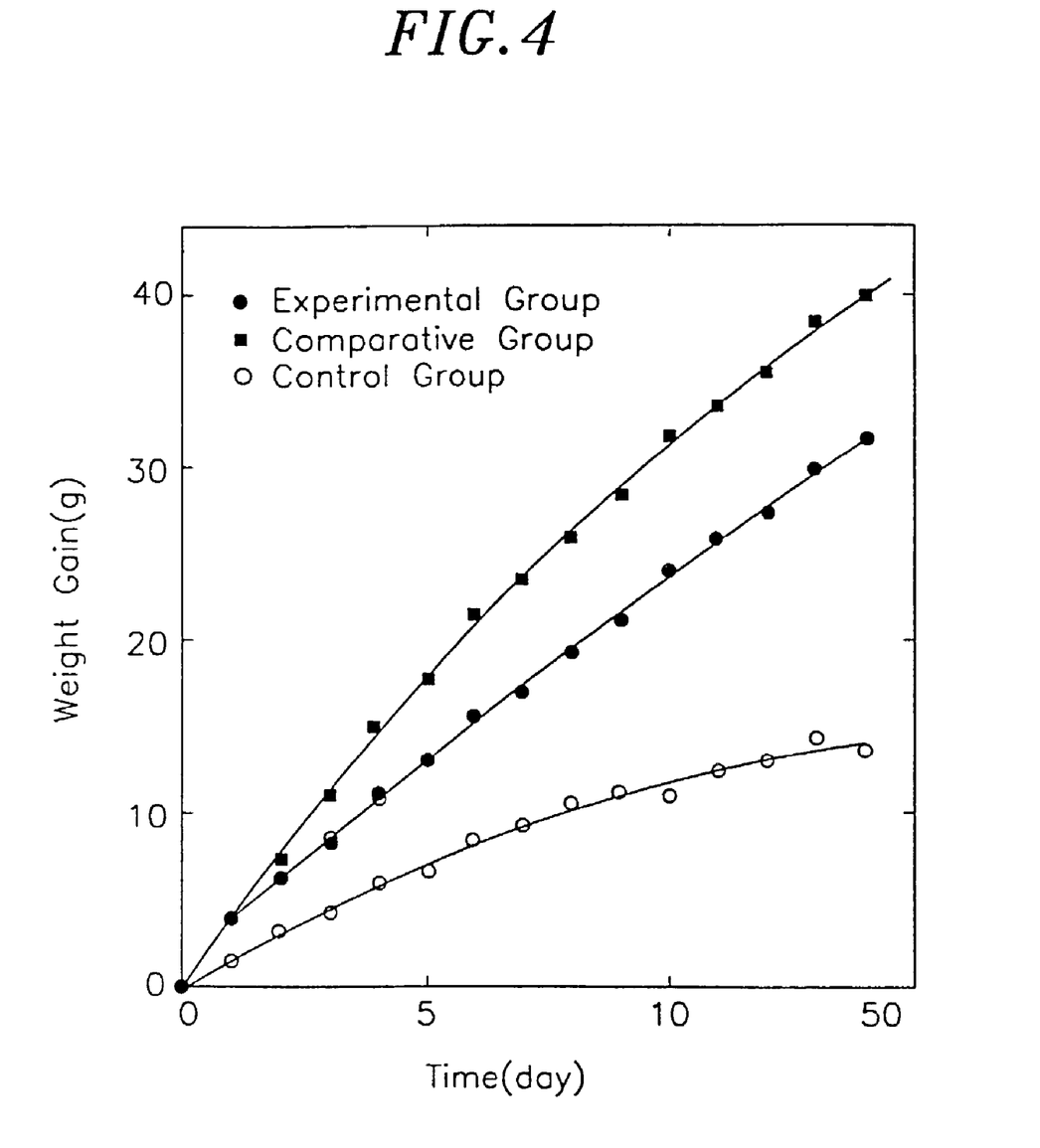
FIG. 4 compares the time-dependent changes in the weight gain pattern of dwarf rats treated with the inventive sustained-release formulation of human growth hormone with those of conventional formulations.

FIG. 4 compares the time-dependent changes in the weight gain pattern, the rats of the Experimental group, the Comparative group and the Control group.

As shown in FIG. 4, the rats of the Experimental group exhibited a continuous weight gain over a period of 2 weeks, which is larger than that of the Comparative group and the Control group. These results show that the inventive microparticle formulation is more effective than the conventional formulations owing to its sustained-release property.

TEST EXAMPLE 4

In vivo Release-Test

The sustained-release microparticle prepared in Example 2 was dispersed in a cottonseed oil so that the concentration of hGH became 1.5 mg/ml.

Twenty-four heads of seven week-old dwarf rats having an average body weight of 105 g were divided into four groups, each consisting of six rats. The rats of the first group were administered by a subcutaneous injection with 0.1 ml of the microparticle dispersion prepared above (corresponding to 150 μg of hGH) every three days for a period of two weeks (Experimental group). The rats of the second group were administered with Eutropin®, under the same condition (Comparative group 1). The rats of the third group were administered with Eutropin® corresponding to 50 µg of hGH daily for a period of two weeks (Comparative group 2). The rats of the fourth group were not administered with hGH (non-treated Control group). The rats were weighted every day to examine the change in their body weight.

Figure 5:
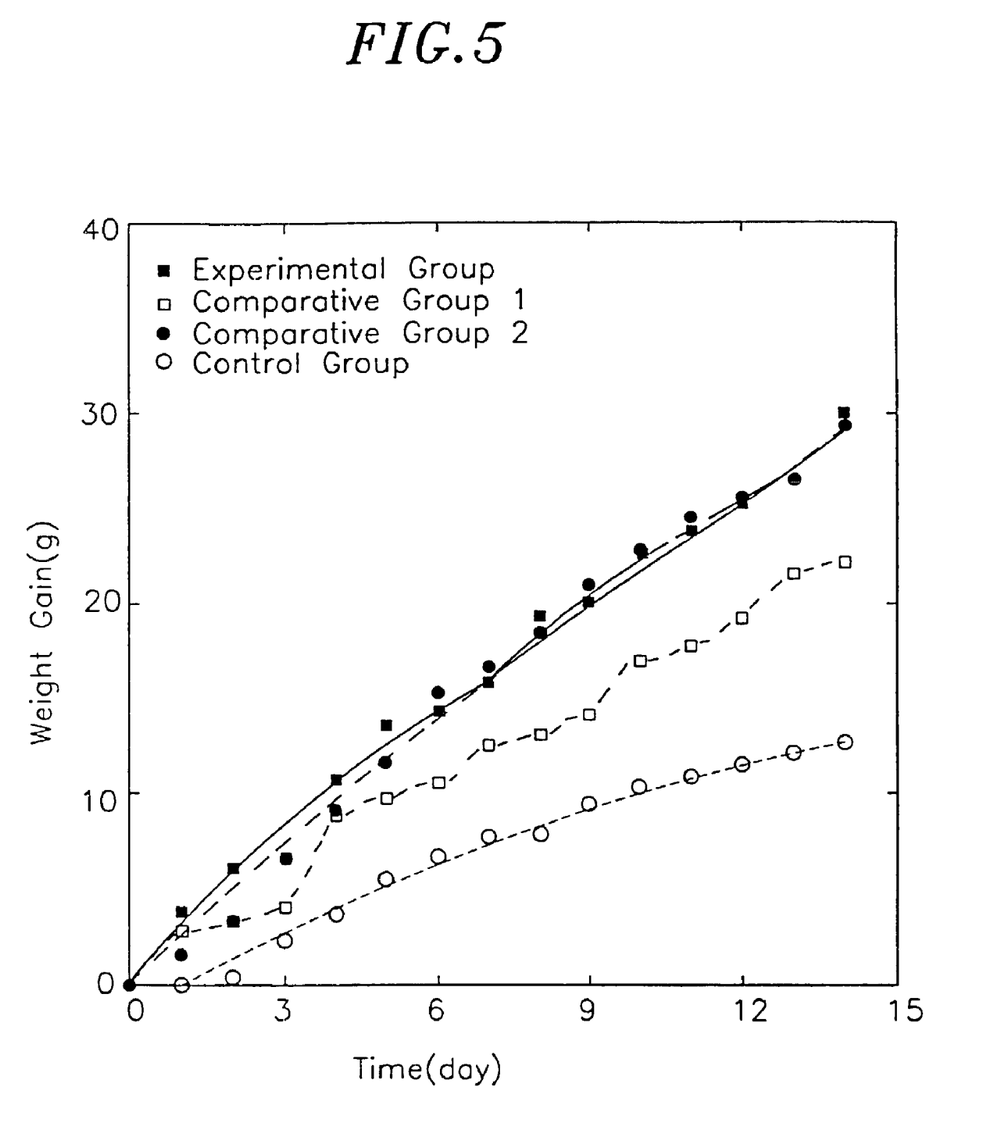
FIG. 5 contrasts the time-dependent changes in the weight gain pattern of dwarf rats treated with the inventive sustained-release formulation of human growth hormone with those of conventional formulations.

FIG. 5 contrasts the time-dependent changes in the weight gain patterns of the Experimental group, the Comparative groups and the Control group.

As shown in FIG. 5, the rats of the Experimental group exhibited a larger weight gain than the rats of the Comparative groups and the Control group. The rats of Comparative group 1 shows significant weight gain at day 1, however, they exhibits lower weight gain than the rats of the Control group at days 2 and 3 after the administration. The rats of the Experimental group and Comparative group 2 show continuous weight gain. These results show that the inventive microparticle formulation has an effective sustained-release property remaining at least for 3 days.

TEST EXAMPLE 5

In vivo Release-Test

The sustained-release microparticle prepared in Example 2 was dispersed in a cottonseed oil so that the concentration of hGH become 1.5 mg/ml. Eight rabbits having an average body weight of 2.5 kg were divided into two groups, each consisting of four rabbits. The rabbits of one group were administered by an injection with the microparticle dispersion prepared above in an amount corresponding to 3,700 µg of hGH (Experimental group). The rabbits of the other group were not administered with hGH (Control group).

After the administration, blood samples were taken from the rabbits daily over a period of 6 days.

The amount of hGH in the blood samples was quantified by RIA (radio-immuno assay) method.

Figure 6:
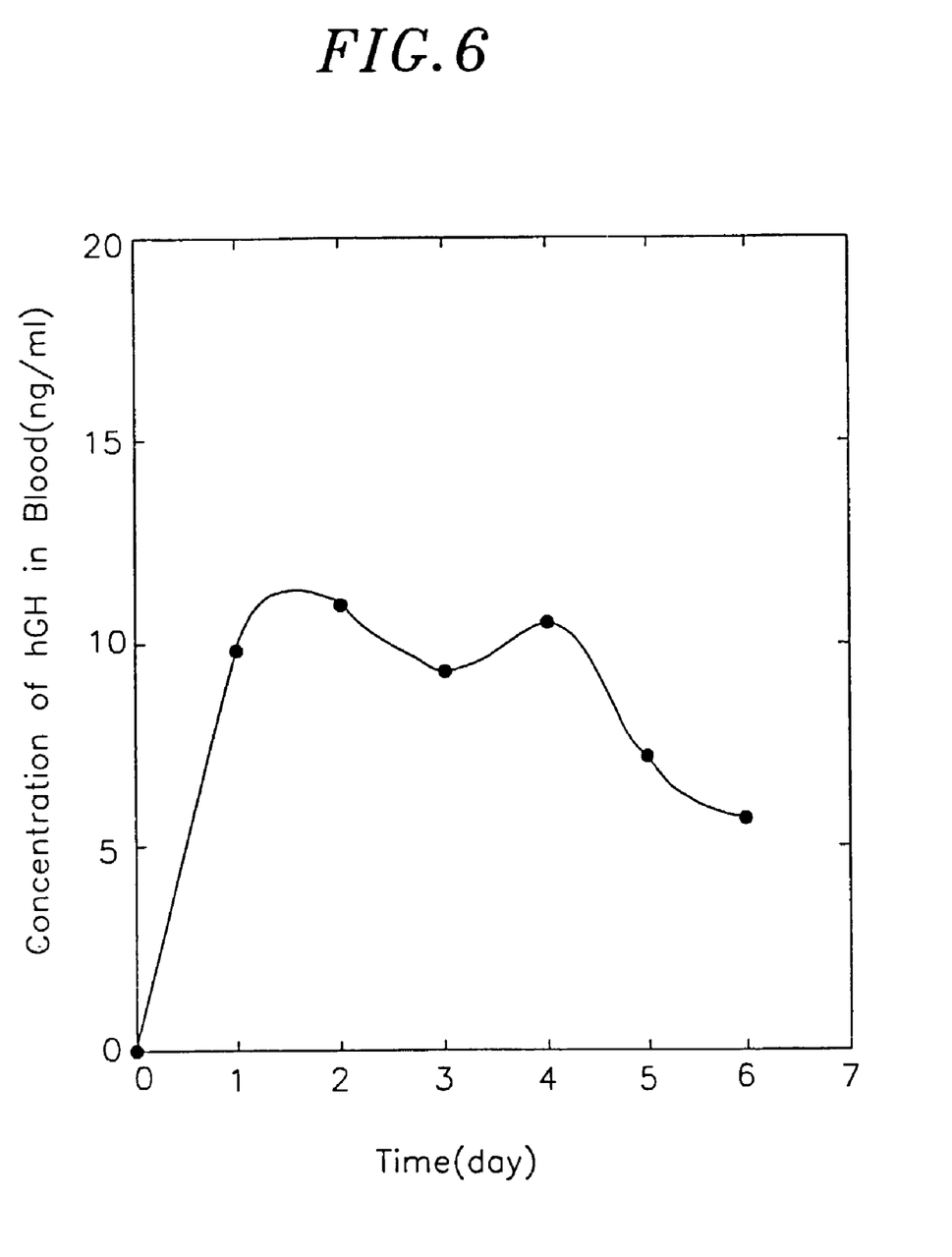
FIG. 6 depicts the time-dependent changes in the concentration of human growth hormone (hGH) in blood.

FIG. 6 depicts the time-dependent changes in the concentration of human growth hormone in blood.

As shown in FIG. 6, the amount of hGH in blood was maintained in a range of from 0 to 11 ng/ml for 4 days after the administration and then was gradually reduced after day 5. This result shows that the inventive microparticle composition have a constant release rate during 4 days and the release rate was gradually reduced thereafter. This result agrees with the result of Test Example 1 wherein the in vivo release rate of hGH is linear until 70% of hGH is release. In contrast, the concentration of hGH in blood of the Control group was under the concentration detectable by RIA method (1 ng/ml) and accordingly can be ignored.

EXAMPLE 4

Preparation of Microparticle and In vitro Release-Test (Step 1) Preparation of Microparticle To a 5 mM PBS containing 2 mg/ml of bovine somatotropin (bST), Tween 80 was added to a concentration of 0.01 wt %. Sodium hyaluronate having a molecular weight of 1,000,000 was added thereto to a concentration of 2mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 µm.

(Step 2) In vitro Release-Test

An in vitro release-test was conducted by employing the microparticles prepared in Step 1 in accordance with the method of Test Example 1 and the stability of the released bST was tested in accordance with the method of Test Example 2.

The released bST was quantified and qualified by way of conducting SEC. As a result, bST was released more than 85% for 72 hours and the denaturation of bGH did not occur.

EXAMPLE 5

Preparation of Microparticle and In vitro Release-Test (Step 1) Preparation of Microparticle To a 5 mM PBS containing 2 mg/ml of porcine somatotropin (pST), Tween 80 was added to a concentration of 0.01 wt %. Sodium hyaluronate having a molecular weight of 1,000,000 was added thereto to a concentration of 2 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 µm.

(Step 2) In vitro Release-Test

An in vitro release-test was conducted by employing the microparticles prepared in Step 1 in accordance with the method of Test Example 1 and the stability of the released pST was tested in accordance with the method of Test Example 2.

The released pST was quantified and qualified by way of conducting SEC. As a result, pST was released more than 90% for 72 hours and the denaturation of pST did not occur.

EXAMPLE 6

Preparation of Microparticle and In vitro Release-Test (Step 1) Preparation of Microparticle To a 5 mM PBS containing 0.4 mg/ml of granulocyte macrophage-colony stimulating factor (GM-CSF), Tween 80 was added to a concentration of 0.01 wt %. Sodium hyaluronate having a molecular weight of 1,000,000 was added thereto to a concentration of 1.6 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 µm.

(Step 2) In vitro Release-Test

An in vitro release-test was conducted by employing the microparticles prepared in Step 1 in accordance with the method of Test Example 1 and the stability of the released GM-CSF was tested in accordance with the method of Test Example 2.

The released GM-CSF was quantified and qualified by way of conducting SEC. As a result, GM-CSF was released more than 92% for 72 hours and the denaturation of GM-CSF did not occur.

EXAMPLE 7

Preparation of Microparticle and In vitro Release-Test (Step 1) Preparation of Microparticle To a 5 mM PBS containing 1000 IU/ml of erythropoietin (EPO) and 0.5 mg/ml of serum albumin, Tween 80 was added to a concentration of 0.01 wt %. Sodium hyaluronate having a molecular weight of 1,000,000 was added thereto to a concentration of 2.5 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.5 μm.

(Step 2) In vitro Release-Test

An in vitro release-test was conducted by employing the microparticles prepared in Step 1 in accordance with the method of Test Example 1 and the stability of the released EPO was tested in accordance with the method of Test Example 2.

The released EPO was quantified and qualified by way of conducting SEC. As a result, EPO was released more than 70% for 72 hours and the denaturation of EPO did not occur.

EXAMPLE 8

Preparation of Microparticle and In vitro Release-Test (Step 1) Preparation of Microparticle To a 5 mM PBS containing $2\times10^5$ IU/ml of interferon-$\alpha$, 0.2 mg/ml of D-mannitol and 0.2 mg/ml of serum albumin, Tween 80 was added to a concentration of 0.01 wt %. Sodium hyaluronate having a molecular weight of 1,000,000 was added thereto to a concentration of 2.5 mg/ml. The resulting solution was supplied to a spray-dryer (Büchi 190) at a rate of 3 ml/min. to prepare microparticles. The temperature of the influx air to the spray dryer was 105° C. The mean diameter of the microparticles thus obtained was 3.5 μm.

(Step 2) In vitro Release-Test

An in vitro release-test was conducted by employing the microparticles prepared in Step 1 in accordance with the method of Test Example 1 and the stability of the released interferon-$\alpha$ was tested in accordance with the method of Test Example 2.

The released interferon-$\alpha$ was quantified and qualified by way of conducting RP-HPLC. As a result, interferon-$\alpha$ was released more than 90% for 72 hours and the denaturation of interferon-$\alpha$ did not occur.

EXAMPLE 9

Preparation of Microparticle and In vitro Release-Test (Step 1) Preparation of Microparticle To a 5 mM PBS containing $2\times10^5$ IU/ml of interferon-$\gamma$, 0.2 mg/ml of glycine and 0.2 mg/ml of serum albumin, Tween 80 was added to a concentration of 0.01 wt %. Sodium hyaluronate having a molecular weight of 1,000,000 was added thereto to a concentration of 2.5 mg/ml. The resulting solution was supplied to a spray-dryer (Büchi 190) at a rate of 3 ml/min. to prepare microparticles. The temperature of the influx air to the spray dryer was 105° C. The mean diameter of the microparticles thus obtained was 3.5 μm.

(Step 2) In vitro Release-Test

An in vitro release-test was conducted by employing the microparticles prepared in Step 1 in accordance with the method of Test Example 1 and the stability of the released interferon-$\gamma$ was tested in accordance with the method of Test Example 2.

The released interferon-$\gamma$ was quantified and qualified by way of conducting RP-HPLC. As a result, interferon-$\gamma$ was released more than 85% for 72 hours and the denaturation of interferon-$\gamma$ did not occur.

EXAMPLE 10

Preparation of Microparticle and In vitro Release-Test (Step 1) Preparation of Microparticles To a 10 mM PBS containing 20 IU/ml of insulin, Tween 80 was added to a concentration of 0.01 wt %. Sodium hyaluronate having a molecular weight of 1,000,000 was added thereto to a concentration of 2 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 μm.

(Step 2) In vitro Release-Test

An in vitro release-test was conducted by employing the microparticles prepared in Step 1 in accordance with the method of Test Example 1 and the stability of the released insulin was tested in accordance with the method of Test Example 2.

The released insulin was quantified and qualified by way of conducting RP-HPLC. As a result, insulin was released more than 95% for 72 hours and the denaturation of insulin did not occur.

EXAMPLE 11

Preparation of Microparticle and In vitro Release-Test (Step 1) Preparation of Microparticle To a 5 mM PBS containing 2 mg/ml of insulin-like growth factor, Tween 80 was added to a concentration of 0.01 wt %. Sodium hyaluronate having a molecular weight of 1,000,000 was added thereto to a concentration of 2 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 μm.

(Step 2) In vitro Release-Test

An in vitro release-test was conducted by employing the microparticles prepared in Step 1 in accordance with the method of Test Example 1 and the stability of the released insulin-like growth factor was tested in accordance with the method of Test Example 2.

The released insulin-like growth factor was quantified and qualified by way of conducting RP-HPLC. As a result, insulin-like growth factor was released more than 90% for 72 hours and the denaturation of insulin-like growth factor did not occur.

COMPARATIVE EXAMPLE 1

Preparation of Gel Formulation and In vitro Release-Test (Step 1) Preparation of Gel Formulation To a 5 mM PBS containing 2.3 mg/ml of hGH, sodium hyaluronate having a molecular weight of 2,000,000 was added to a concentration of 20 mg/ml to obtain 2% hyaluronate gel formulation containing hGH.

(Step 2) In vitro Release-Test

The gel formulation prepared in Step 1 was tested by the procedure of Test Example 1. As a result, 100% of hGH was released within 1 hour. This result shows that the gel formulation releases a drug within a shorter period than the inventive microparticles because it is easily diluted by water.

COMPARATIVE EXAMPLE 2

Preparation of Gel Formulation and In vivo Release-Test (Step 1) Preparation of Gel Formulation To a 5 mM PBS containing 1.5 mg/ml of hGH, sodium hyaluronate having a molecular weight of 2,000,000 was added to a concentration of 20 mg/ml to obtain a non-fluid gel formulation containing hGH.

1 ml of the gel formulation thus obtained was dispersed in 2 ml of cottonseed oil and the mixture was homogenized to form an emulsion.

(Step 2) In vitro Release-Test

Twenty-four heads of seven week-old dwarf rats having an average body weight of 95 g were divided into four groups, each consisting of 6 rats. The rats of one group were administered by a subcutaneous injection with the 0.3 ml of the emulsion prepared in Step 1 (corresponding to 150 μg of hGH) (Group 1).

In order to compare the efficiency of the emulsion formulation with other formulations, the rats of another two groups were administered with a dispersion containing the sustained-release microparticles prepared in Example 2 dispersed in a cottonseed oil so that the concentration of hGH became 150 μg (Group 2); Eutropin® corresponding to 150 μg of hGH (Group 3), respectively. The rats of the last group were not administered with hGH formulation (Control group). After the administration, the changes in the weight gain of the rats were observed for 6 days.

Figure 7:
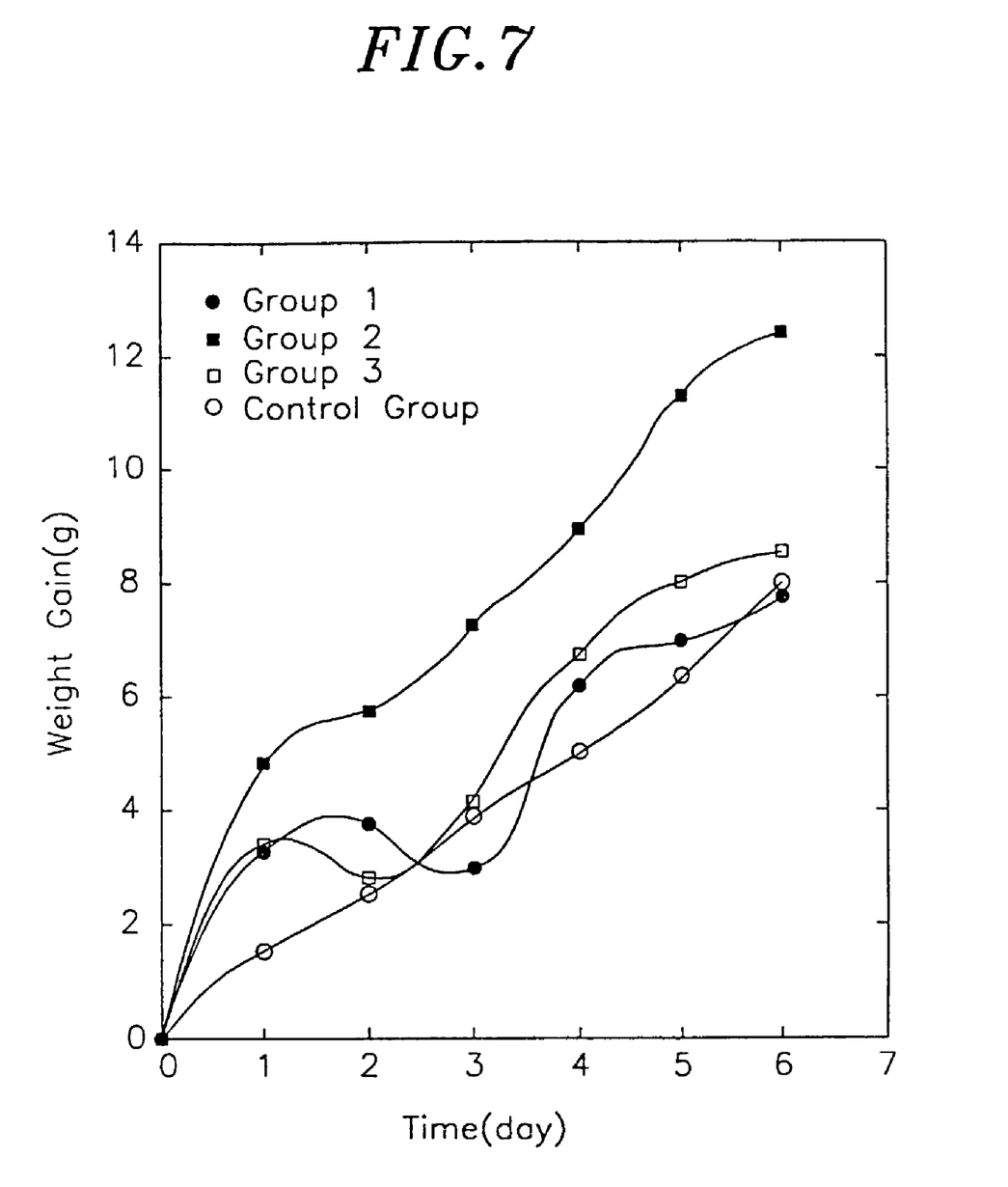
FIG. 7 describes the time-dependent changes in the weight gain pattern of dwarf rats treated with the inventive sustained-release formulation of human growth hormone in comparison with those of conventional formulations.

FIG. 7 describes the time-dependent changes in the weight gain patterns of dwarf rats treated with the inventive sustained-release formulation of human growth hormone in comparison with those of conventional formulations. As a result, the time-dependent changes in the weight gain pattern of dwarf rats treated with the hyaluronate gel formulation were similar to the Eutropin® group. That is, the body weight of dwarf rats treated with the hyaluronate gel formulation was reduced 2 or 3 days after the administration and was similar to that of the rats of the Control group thereafter. However, rats of the group treated with the inventive formulation exhibited continuous weight gain higher than the other groups by 150% during 6 days.

COMPARATIVE EXAMPLE 3

Preparation of Microparticle Formulation using Sodium-Carboxymethyl Cellulose and In vivo and In vitro Release-Test (Step 1) Preparation of Microparticle Formulation To a 5 mM PBS containing 0.2 mg/ml of hGH, Tween 80 was added to a concentration of 0.01 wt %. Sodium-carboxymethyl cellulose (Na-CMC, medium viscosity grade) was added thereto to a concentration of 1.8 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 μm.

(Step 2) In vitro Release-Test

The microparticle formulation prepared in Step 1 was tested by the procedure of Test Example 1 and the results are listed in Table 1.

TABLE 1

| Time(hour) | 0 | 1 | 3 | 5 | 7 | 24 | 48 | 72 | 144 |
|---|---|---|---|---|---|---|---|---|---|
| Released Amount of hGH(%) | 0 | 32 | 40 | 48 | 52 | 57 | 63 | 65 | 65 |

As shown in Table 1, the time-dependent changes in the in vitro release pattern of the microparticle formulation prepared in Step 1 differ from that of the inventive microparticle. That is, it exhibited the ill-balanced release pattern that more than 30% of hGH was released during initial 1 hour, another 30% was released until 48 hours, and then release of hGH hardly occurred thereafter. These results show that the release pattern of a drug becomes ill-balanced by the interaction between the protein drug and the matrix, and possibility of the denaturation of the drug is very high, when a natural carbohydrate polymer having a hydrophobicity stronger than hyaluronic acid is used as a matrix material.

(Step 3) In vivo Release-Test

The microparticle formulation prepared in Step 1 was dispersed in a cottonseed oil. The resulting dispersion was administered to 7 week-old dwarf rats in an amount of 300 μg of hGH per head and a non-administered group were used as a Control group. The weight gains of rats were measured over a period of 7 days and the results are listed in Table 2 as an accumulated weight gain.

TABLE 2

| Time(day) | day 1 | day 2 | day 3 | day 4 | day 5 | day 6 | day 7 |
|---|---|---|---|---|---|---|---|
| Control group | 0.6 | 0.8 | 3.3 | 5.5 | 7.6 | 6.7 | 7.4 |
| Na-CMC formulation group | 5.2 | 3.3 | 6.4 | 8.3 | 10.5 | 9.4 | 9.0 |

As shown in Table 2, the rats treated with the microparticle prepared in Step 1 exhibited the weight gain pattern similar to that of the hyaluronate-gel formulation in Comparative Example 2. That is, they exhibited the weight gain only at day 1 and the body weight thereof was reduced at day 2. Further, they exhibited the weight gain rate lower than the Control group thereafter, and finally show a weight gain similar to the Control group at day 7. These results show that the Na-CMC formulation has an inferior release property and titer than the inventive hyaluronate microparticle, although Na-CMC is a natural carbohydrate polymer as hyaluronic acid is.

COMPARATIVE EXAMPLE 4

Preparation of Microparticle Formulation using hyaluronic Acid-Benzyl Ester and In vivo and In vitro Release-Test (Step 1) Preparation of Microparticle Formulation Natural hyaluronic acid and benzyl alcohol were chemically reacted to produce hyaluronic acid-benzyl ester and then microparticles containing hGH was prepared as described below.

To a 5 mM PBS containing 2 mg/ml of hGH, Tween 80 was added to a concentration of 0.01 wt %. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 2.5 µm.

The particles thus obtained was dispersed in dimethylsulfoxide (DMSO) containing 6% of hyaluronic acid-benzyl ester and the resulting dispersion was added to mineral oil containing a surfactant, Aracel ATM (ICI, U.S.A.), and the mixture was homogenized to form a microemulsion. The resulting microemulsion consists of a continuous phase of mineral oil and a dispersive phase of hyaluronic acid-benzyl ester/DMSO solution containing hGH dispersed therein.

Ethyl acetate was added to the microemulsion thus obtained with stirring and then DMSO was extracted with ethyl acetate and hyaluronic acid-benzyl ester becomes hardened to produce hyaluronic acid-benzyl ester particles containing hGH particle. The mean diameter of the final particles thus obtained was 5.5 µm and the content of hGH was 45%.

(Step 2) In vivo Release-Test

The microparticles prepared in step 1 were tested by the procedure of Test Example 1 and the results are listed in Table 3.

TABLE 3

| Time(hour) | 0 | 1 | 3 | 5 | 7 | 24 | 48 | 72 | 144 |
|---|---|---|---|---|---|---|---|---|---|
| Released Amount of hGH(%) | 0 | 15 | 21 | 23 | 25 | 27 | 28 | 30 | 30 |

As shown in Table 3, in the microparticle prepared by endowing hydrophobicity to the natural hyaluronic acid by using hyaluronic acid-benzyl ester, release of hGH was hardly occurred after initial 5 hours. The reason why hGH was not released is that the interaction between the protein drug (hGH) and hyaluronic acid-benzyl ester matrix is too strong.

(Step 3) In vivo Release-Test

The microparticles prepared in step 1 were dispersed in a cottonseed oil. The resulting dispersion was administered to 7 week-old dwarf rats in an amount of 300 µg of hGH per head and a non-administered group were used as a Control group. The weight gains of rats were measured over a period of 7 days and the results are listed in Table 4 as an accumulated weight gain.

TABLE 4

| Time(day) | Day 1 | day 2 | day 3 | day 4 | day 5 | day 6 | day 7 |
|---|---|---|---|---|---|---|---|
| A | 1.2 | 2.3 | 3.6 | 5.7 | 6.6 | 7.3 | 8.2 |
| B | 3.6 | 2.7 | 5.4 | 6.3 | 7.1 | 8.4 | 8.0 |

A: Control group
B: hyaluronic acid-benzyl ester microparticle formulation group As shown in Table 4, the hyaluronic acid-benzyl ester microparticle formulation has hardly an efficiency after day 1.

COMPARATIVE EXAMPLE 5

Preparation of Microparticle and In vitro Release-Test (Step 1) Preparation of Gel Formulation To a 5 mM PBS containing 1 mg/ml of hGH, Tween 80 was added to a concentration of 0.01 wt %. Sodium hyaluronate having a molecular weight of 100,000 was added to a concentration of 1 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 µm.

(Step 2) In vitro Release-Test

An in vitro release test was conducted by employing the microparticles prepared in Step 1 in accordance with the method of Test Example 1. The result showed that 100% of hGH was released within 1 hour. Thus, the microparticle prepared by using sodium hyaluronate having a low molecular weight releases the drug within a much shorter period than the inventive microparticles because it is readily solubilized in water.

COMPARATIVE EXAMPLE 6

Preparation of Microparticle and In vitro Release-Test (Step 1) Preparation of Gel Formulation To a 5 mM PBS containing 1 mg/ml of hGH, Tween 80 was added to a concentration of 0.01 wt %. Sodium hyaluronate having a molecular weight of 500,000 was added to a concentration of 1 mg/ml. The resulting solution was supplied to a spray-dryer (Büchi 190) at a rate of 3 ml/min. to prepare microparticles. The temperature of the influx air to the spray dryer was 85° C. The mean diameter of the microparticles thus obtained was 3.0 µm.

(Step 2) In vitro Release-Test

An in vitro release test was conducted by employing the microparticles prepared in Step 1 in accordance with the method of Test Example 1. The result showed that 100% of hGH was released within 1 hour. Thus, the microparticle prepared by using sodium hyaluronate having a low molecular weight releases the drug within a much shorter period than the inventive microparticles because it is readily solubilized in water.

While the invention has been described with respect to the above specific embodiments, it should be recognized that various modifications and changes may be made and also fall within the scope of the invention as defined by the claims that follow.

What is claimed is:

1. A sustained-release drug composition comprising solid micorparticles consisting essentially of water-soluble hyaluronic acid having a weight greater than 2,000,000 Da or an inorganic salt thereof, and a protein or peptide drug and a stabilizer, wherein the average size of the micorparticles range from 0.1 to 40 μm and the protein or peptide drug and the stabilizer are encased in the micorparticle of hyluronic acid or an inorganic salt thereof.

2. The composition of claim 1, wherein the molecular weight of hyaluronic acid ranges from greater than 2,000,000 Da to 3,200,000 Da.

3. The composition of claim 1, wherein the average size of microparticle ranges from 1 to 10 μm.

4. The composition of claim 1, wherein the drug is selected from the group consisting of human growth hormone, bovine somatotropin, porcine somatotropin, growth hormone releasing hormone, growth hormone releasing peptide, granulocyte-colony stimulating factor, granulocyte macrophage-colony stimulating factor, macrophage-colony stimulating factor, erythropoietin, bone morphogenetic protein, interferon, insulin, atriopeptin-III, monoclonal antibody, TNF, macrophage activating factor, interleukin, tumor denaturing factor, insulin-like growth factor, epidermal growth factor, tissue plasminogen activator, urokinase and a mixture thereof.

5. The composition of claim 1, wherein the inorganic salt is selected from the group consisting of sodium, potassium, lithium, calcium, ammonium, magnesium, zinc, copper and cobalt salts of hyaluronic acid.

6. The composition of claim 1, wherein the stabilizer is selected from the group consisting of a polysaccharide, protein, amino acid, lipid, fatty acid, inorganic salt, surfactant and a mixture thereof.

7. An injection formulation comprising the sustained-release composition of claim 1 dispersed in an injection medium.

8. The injection formulation of claim 7 further comprising a dispersant or preservative.

9. The injection formulation of claim 7, wherein the injection medium is selected from the group consisting of a buffered aqueous solution, ethanol, propyleneglycol, polyethyleneglycol, vegetable oil, mineral oil, squalene, cod liver oil, mono-, di- and tri-glycerid and a mixture thereof.

10. The injection formulation of claim 9, wherein the vegetable oil is selected from the group consisting of corn oil, olive oil, soy bean oil, safflower oil, cottonseed oil, sesame oil, coconut oil, castor oil and mixture thereof.

11. An aerosol formulation comprising the sustained-release composition of claim 1.

* * * * *